United States Patent [19]
Weissig et al.

[11] Patent Number: 6,090,619
[45] Date of Patent: Jul. 18, 2000

[54] MATERIALS AND METHODS FOR INTRACELLULAR DELIVERY OF BIOLOGICALLY ACTIVE MOLECULES

[75] Inventors: Volkmar Weissig, Allston, Mass.; Jeffrey Allen Hughes, Gainesville, Fla.; Jurgen Lasch, Halle, Germany; Thomas Cardon Rowe, Gainesville, Fla.

[73] Assignee: University of Florida, Gainesville, Fla.

[21] Appl. No.: 08/929,175

[22] Filed: Sep. 8, 1997

[51] Int. Cl.$^7$ .............................. C12N 15/00; A61K 48/00
[52] U.S. Cl. ...................... 435/320.1; 435/91.4; 435/325; 435/455; 514/44; 514/642; 536/23.1
[58] Field of Search .................................. 435/455, 458, 435/320.1, 91.4, 325; 514/44, 642; 536/23.1

[56] References Cited

U.S. PATENT DOCUMENTS

| | | | |
|---|---|---|---|
| 5,277,897 | 1/1994 | Piwnica-Worms et al. | 424/1.65 |
| 5,527,928 | 6/1996 | Nantz et al. | 554/105 |
| 5,569,754 | 10/1996 | Williams et al. | 536/23.5 |
| 5,674,908 | 10/1997 | Haces et al. | 514/642 |

FOREIGN PATENT DOCUMENTS 9534647  12/1995  WIPO .

OTHER PUBLICATIONS

Webster's II New Riverside University Dictionary, p. 67, col. 2, 1994.
Collombet et al., (Molecular Medicine Today, vol. 4, 1:31–38), 1998.
Seibel et al. (Nucleic acids Res. vol. 23, 1, 10–17, 1995).
Murphy Trends in Biotechnology, 15, 8, 326–30, 1997.
Weissig, Volkmar, Jürgen Lasch, Gregory Erdos, Helmut W. Meyer, Thomas C. Rowe, Jeffrey Hughes (1998) "DQAsomes: A Novel Potential Drug and Gene Delivery System Made from Dequalinium™" *Pharmaceutical Research* 15(2):334–337.
Ledley, Fred D. (1996) "Pharmaceutical Approach to Somatic Gene Therapy" *Pharmaceutical Research* 13(11):1595–1614.
Capecchi, Mario R. (1980) "High Efficiency Transformation by Direct Microinjection of DNA into Cultured Mammalian Cells" *Cell* 22:479–488.
Weiss et al. (1987) "Dequalinium, a topical antimicrobial agent, displays anticarcinoma activity based on selective mitochondrial acculation" *Proc. Natl. Acad. Sci. USA* 84:5444–5448.
Sompayrac, Lauren M. and Kathleen J. Danna (1981) "Efficient infection of monkey cells with DNA of simian virus 40" *Proc. Natl. Acad. Sci. USA* 78(12):7575–7578.
Rotenberg, Susan A., Stephen Smiley, Marius Ueffing, Robert S. Krauss, Lan Bo Chen, I. Bernard Weinstein (1990) "Inhibition of Rodent Protein Kinase C by the Anticarcinoma Agent Dequalinium" *Cancer Research* 50:677–685.

Chen, Claudia and Hiroto Okayama (1987) "High–Efficiency Transformation of Mammalian Cells by Plasmid DNA" *Molecular and Cellular Biology* 7(8):2745–2752.
Chang, David D. and David A. Clayton (1987) "A Mammalian Mitochondrial RNA Processing Activity Contains Nucleus–Encoded RNA" *Science* 235:1178–1184.
Zhou, Shaoqui and William S. Allison (1988) "Inhibition And Photoinactivation Of The Bovine Heart Mitochondrial $F_1$–A Tphase By The Cytotoxic Agent, Dequalinium" *Biochemical and Biophusical Research Communications* 152(3):968–972.
Vercesi et al. (1991) "Digitonin Permeabilization Does Not Affect Mitochondrial Function And Allows The Determination Of The Mitochondrial Membrane Potential of *Trypanosoma cruzi* in Situ" *J. Biological Chemistry* 266(22):14431–14434.
Vestweber, Dietmar and Gottfried Schatz (1989) "DNA–protein conjugates can enter mitochondria via the protein import pathway" *Nature* 338:170–172.
Seibel et al. (1995) "Transfection of mitochondria: strategy towards a gene therapy of mitochondrial DNA diseases" *Nucleic Acids Research* 23(1):10–17.
Johnson, Lincoln V., Marcia L. Walsh, Beverly J. Bockus, Lan Bo Chen (1981) "Monitoring of Relative Mitochondrial Membrane Potential in Living Cells by Fluorescence Microscopy" *J. of Cell Biology* 88:526–535.
Li et al. (1994) "Subcellular Partitioning of MRP RNA Assessed by Ultrastructural and Biochemical Analysis" *J. of Cell Biology* 124(6):871–882.
Bodden, William L., Sanjeewani T. Palayoor, William N. Hait (1986) "Selective Antimitochondrial Agents Inhibit Calmodulin" *Biochemical and Biophysical Research* 135(2):574–582.
Schreier et al. (1992) "Toxin And Gene Delivery With Artificial Viral Envelopes In Vitro" *Proceed. Intern. Symp. Control Rel. Bioact. Mater* 19:70–71.
Wallace, Douglas C. (1994) "Mitochondrial DNA Mutations in Diseases of Energy Metabolism" *J. of Bioenergetics and Biomembranes* 26(3):241–250.
Aubin, Rémy J., Michael Weinfeld, Malcolm C. Paterson (1988) "Factors Influencing Efficiency and Reproducibilty of Polybrene–Assisted Gene Transfer" *Somatic Cell and Molecular Genetics* 14(2):155–167.

(List continued on next page.)

*Primary Examiner*—Scott D. Priebe
*Assistant Examiner*—Dave Trong Nguyen
*Attorney, Agent, or Firm*—Saliwanchik, Lloyd & Saliwanchik

[57] ABSTRACT

The subject invention finds utility in the area of gene therapy of diseases. More specifically, the invention concerns the making of a novel non-viral vector which can bind to desired DNA to form a combination useful to transfect diseased mitochondria of human or animal cells. The non-viral vector comprises a dequalinium salt subjected to standard liposome production procedures to obtain the vector named DQAsomes.

3 Claims, 4 Drawing Sheets

OTHER PUBLICATIONS

Babbs, M., H.O.J. Collier, W.C. Austin, M.D. Potter, E.P. Taylor (1955) "Salts Of Decamethylene–BIS–4–Aminoquinaldinium "Dequadin"), A New Antimicrobial Agent" J. Pharm. Pharmacol. 8:110–119.

Ledley, Fred D. (1994) "Non–viral gene therapy" Current Opinion in Biotechnology 5:626–636.

Schreier, Hans, Michael Ausborn, Susanne Gunther, Volkmar Weissig, Ramesh Chander (1995) "(Patho)physiologic Pathways to Drug Targeting: Artificial Viral Envelopes" J. Molecular Recognition 8:59–62.

Kabanov, A.V. and V.A. Kabanov (1995) "DNA Complexes with Polycations for the Delivery of Genetic Material into Cells" Bioconjugate Chem. 6(1):7–20.

Ledley, Fred D. (1995) "Nonviral Gene Therapy: The Promise of Genes as Pharmaceutical Products" Human Gene Therapy 6:1129–1144.

Dunn, Philip M. (1994) "Dequalinium, a selective blocker of the slow afterhyperpolarization in rat sympathetic neurones in culture" European Journal of Pharmacology 252:189–194.

Steichen, John D., Michael J. Weiss, David R. Elmaleh, Robert L. Martuza (1991) "Enhanced in vitro uptake and retention of $^3$H–tetraphenylphosphonium by nervous system tumor cell" J. Neurosurg 74:116–122.

Christman, J. Eric, David S. Miller, Peter Coward, Lloyd H. Smith, Nelson N.H. Teng (1990) "Study of the Selective Cytotoxic Properties of Cationic, Lipophilic Mitochondrial–Specific Compounds in Gynecologic Malignancies" Gynecologic Oncology 39:72–79.

Neumann, E., M. Schaefer–Ridder, Y. Wang, P.H. Hofschneider (1982) "Gene transfer into mouse lyoma cells by electroporation in high electric fields" The EMBO Journal 1(7):841–845.

Dequalinium chloride

↓ 1) make film
2) add water

DQAsomes

Plasmid DNA : DQAsome Complex

<u>The transfecting species</u>

MATERIALS AND METHODS FOR INTRACELLULAR DELIVERY OF BIOLOGICALLY ACTIVE MOLECULES

The subject invention was made with government support under a research project supported by NIH Grant Nos. RO 1-GM-47535; R29-HL55770-02 and PO1-AG10485-06. The government has certain rights in this invention.

BACKGROUND OF THE INVENTION

Since the first demonstration in 1988 that mitochondrial DNA (mtDNA) base substitution and deletion mutations are linked to human disease, a variety of degenerative diseases have been associated with mtDNA mutations (reviewed in Wallace, D. C. [1994] *J. Bioenergetics and Biomembranes* 26:241–250). For example, certain deleterious base substitutions can cause familial deafness and some cases of Alzheimer's disease and Parkinson's disease. Other nucleotide substitutions have been associated with Leber's Hereditary Optic Neuropathy (LHON) and myoclonic epilepsy and ragged-red fiber disease (MERF). Base substitutions can also cause pediatric diseases such as Leigh's syndrome and dystonia. Severe rearrangements involving deletions have been linked with adult-onset chronic progressive external ophthalmoplegia(CPEO) and Kearns-Sayre syndrome (KSS) as well as the lethal childhood disorder Pearson's marrow/pancreas syndrome (Wallace [1994], supra).

Somatic gene therapy. Three different approaches for somatic gene therapy (reviewed in Ledley, F. D. [1996] *Pharmaceutical Res.* 13:1996) can be distinguished based on the nature of the material that is administered to the patient: (a) cell-based approaches involving the administration to the patient of genetically engineered cells ("ex-vivo"), (b) administration to the patient of genetically engineered, attenuated, or defective viruses, and (c) plasmid-based approaches that involve pharmaceutical formulations of DNA molecules. A variety of viral and non-viral methods have been developed for introducing DNA molecules into a cell. Non-viral techniques include precipitation of DNA with calcium phosphate (Chen, C., H. Okayama [1987] *Mol. Cell. Biol.* 7:2745–2752), dextran derivatives (Sompayrac, L., K. Danna [1981] *PNAS* 12:7575–7584), or polybrene (Aubin, R. J., M. Weinfield, M. C. Paterson [1988] *Somatic Cell Mol. Genet.* 14:155–167); direct introduction of DNA using cell electroporation (Neuman, E., M. Schaefer-Ridder, Y. Wang, P. H. Hofschneider[1982] *EMBO J.* 1:841–845) or DNA microinjection(Capecchi, M. R. [1980] *Cell* 22:479–486); complexation of DNA with polycations (Kabanov, A. V., V. A. Kabanov [1995] *Bioconjugate Chem.* 6:7–20); and DNA incorporation in reconstructed virus coats (Schreier, H., R. Chander, V. Weissig et al. [1992] *Proceed. Intern. Symp. Control. Rel. Bioact. Mater.* 19:70–71; Schreier, H., M. Ausborn, S. Guinther, V. Weissig, R. Chander [1995] *J. Molecular Recog.* 8:59–62).

Cationic lipids have become important reagents for gene transfer in vitro and in vivo. Several clinical trials approved by the NIH are in progress (reviewed in Ledley, F. D. [1994] *Current Opinion in Biotechnology* 5:626–636; and Ledley, F. D. [1995] *Human Gene Therapy* 6:1129–1144). In terms of transfection efficiency, virus-based vectors are superior to all other DNA transfection methods. Several different viral vectors have been developed and are in clinical trials including those derived from murine leukemia viruses (retroviruses), adeno-associatedvirus, and adenovirus (reviewed in Ledley [1996], supra).

Transfection of mitochondria. There have been only a few reports of nucleic acids entering mitochondria, and most have focused on the nuclear encoded RNA component of the mitochondrial RNA processing activity, RNase MRP (Chang, D. D., D. A. Clayton [1987] *Science* 235:1178–1184; and Li, K., C. S. Smagula, W. J. Parsons et al. [1994] *J. Cell. Biol.* 124:871–882). The uptake of exogenous DNA into mitochondria involving the protein import pathway has been reported from two laboratories. Vestweber and Schatz ([1989] *Nature* (London) 338:170–172) achieved uptake of a 24-bp both single- and double-strandedoligonucleotide into yeast mitochondriaby coupling the 5' end of the oligonucleotide to a precursor protein consisting of the yeast cytochrome c oxidase subunit IV presequence fused to a modified mouse dihydrofolate reductase. More recently, Seibel et al. (1995, *Nucleic Acids Research* 23:10–17) reported the import into the mitochondrial matrix of double-stranded DNA molecules conjugated to the amino-terminal leader peptide of the rat ornithine-transcarbamylase. Both studies, however, were done with isolated mitochondria not addressing the question of how oligonucleotide-peptide conjugates will pass the cytosolic membrane and reach mitochondrial proximity. Negatively-charged biological cell surfaces and lysosomal degradation establish major obstacles which are very unlikely to be overcome by single oligonucleotide-peptide complexes.

Dequalinium. Dequalinium (DQA) (Babbs, M., H. O. J. Collier, W. C. Austin et al. [1955] *J. Pharm. Pharmacol.* 8:110–119)has been used for over 30 years as a topical antimicrobial agent. There is no consensus about the molecular target of DQA; several different targets such as the small conductance $Ca^{2+}$-activated $K^+$ channel, F1-ATPase, calmodulin, and proteinase K have been suggested (Dunn, P. M. [1994] *Eur. J Pharmacology* 252:189–194; Zhuo, S., W. S. Allison [1988] *Biochem. Biophys. Res. Comm.* 152:968–972; Bodden, W. L., S. P. Palayoor, W. N. Hait [1986] *Biochem. Biophys. Res. Comm.* 135:574–582; Rotenberg, S. A., S. Smiley, M. Ueffing et al. [1990] *Cancer Res.* 50:677–685). DQA is an amphiphilic dicationic compound resembling bolaform electrolytes, that is, they are symmetrical molecules with two charge centers separated at a relatively large distance. Lipophilic cations are known to localize in mitochondria of living cells as a result of the electric potential across the mitochondrial membrane (Johnson, L. V., M. L. Walsh, B. J. Bockus, L. B. Chen [1981] *J. Cell. Biol.* 88:526–535). The accumulation of DQA in mitochondria has been reported (Weiss, M. J., J. R. Wong, C. S. Ha et al. [1987] *PNAS* 84:5444–5448; Christman, E. J., D. S. Miller, P. Coward et al. [1990] *Gynecol. Oncol.* 39:72–79; Steichen, J. D., M. J. Weiss, D. R. Elmaleh, R. L. Martuza [1991]*J. Neurosurg.* 74:116–122; Vercesi, A. E., C. F. Bernardes, M. E. Hoffman et al. [1991]*J. Biol. Chem.* 266:14431–14434).

Despite the progress being made in developing viral and non-viral DNA delivery systems, there is a need for an efficient method for introducing DNA into mitochondria of intact cells.

BRIEF SUMMARY OF THE INVENTION

The subject invention pertains to materials and methods for selectively and specifically delivering biologically active molecules to the mitochondria. In a preferred embodiment, DNA or other polynucleotide sequence can be delivered to the mitochondria as part of a gene therapy procedure.

The subject invention pertains to the delivery to the mitochondria of a complex of DNA with a molecule having two positive charge centers separated by a hydrocarbon chain. In a specific embodiment, the subject invention concerns the transformation of a salt of dequalinium (DQA) into an effective non-viral gene therapy vector. DQA is complexed with DNA as described herein to form an effective vehicle for delivering DNA to the mitochondria. These DQA-DNA complexes are referred to herein as DQAsomes. The DQAsomes can be used effectively as described herein as a transfection system. This system is especially useful in gene therapy to treat diseases associated with abnormalities in mitochondrial DNA.

DETAILED DISCLOSURE OF THE INVENTION

The subject invention provides materials and methods useful in delivering biologically active molecules to mitochondria. In a preferred embodiment, the subject invention provides a method for selectively transforming mitochondrial DNA. This method can be used to correct defects in mitochondrial DNA.

In a specific embodiment, the subject invention pertains to the use of an amphiphilic dicationic compound complexed with DNA to deliver the DNA specifically to the mitochondria. In a preferred embodiment, the amphiphilic dicationic compound is a salt of dequalinium (DQA). The salt may be, for example, dequalinium chloride (available from Sigma Chemical Company, St. Louis, Mo.). Using standard liposome production procedures, combined with the teachings provided herein, dequalinium chloride can be transformed into an effective non-viral gene therapy vector (DQAsomes). This is a novel use for DQA. This is the first disclosure that DQAsomes are effective as a transfection system.

The gene therapy vectors of the subject invention can be used to treat diseases associated with mitochondrial DNA, for example, Alzheimer's disease, Parkinson's disease, Leber's Hereditary Optic Neuropathy, myoclonic epilepsy and ragged-red fiber disease, Leigh's syndrome dystonia, adult-onset chronic progressive external ophthalmoplegia, Kearns-Sayre syndrome and Pearson's marrow/pancreas syndrome. The DNA delivery vectors of the subject invention are particularly advantageous because these amphipathic dicationic compounds will specifically deliver DNA to the mitochondria. Thus, in a specific embodiment of the subject invention, DQAsomes can be used as a mitochondria-specific polynucleotide delivery system.

Those skilled in the art, having the benefit of the instant disclosure, will appreciate that other salts of dequalinium can be used. In one specific embodiment, dequalinium acetate (Sigma Chemical Company, St. Louis, Mo.) can be used. Other amphiphilic dicationic compounds which can be used according to the subject invention include all derivatives of dequalinium with varying substituents at the aromatic ring systems including 1-1'-Decamethylene bisquinolinium-salts, which have no substituents at all. The critical characteristics of the compounds which can be used according to the subject invention include the presence of two positive charge centers separated by a relatively long hydrocarbon chain. The hydrocarbon chain may have, for example, from about 5 to about 20 carbons. In a preferred embodiment, the hydrocarbon chain may have from about 8 to about 12 carbons.

Following are examples which illustrate procedures for practicing the invention. These examples should not be construed as limiting. All percentages are by weight and all solvent mixture proportions are by volume unless otherwise noted.

EXAMPLE 1

Preparation of DQAsomes

Figure 1:
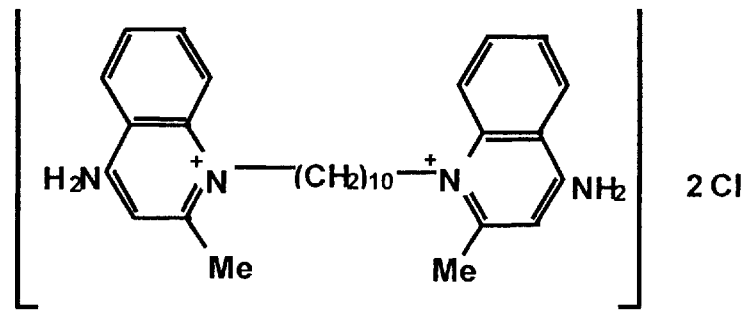
FIG. 1 shows the production of DQAsomes and the interaction with plasmid DNA. The DQAsomes can be produced utilizing standard liposome methods in conjunction with the teachings provided herein.
Figure 1:
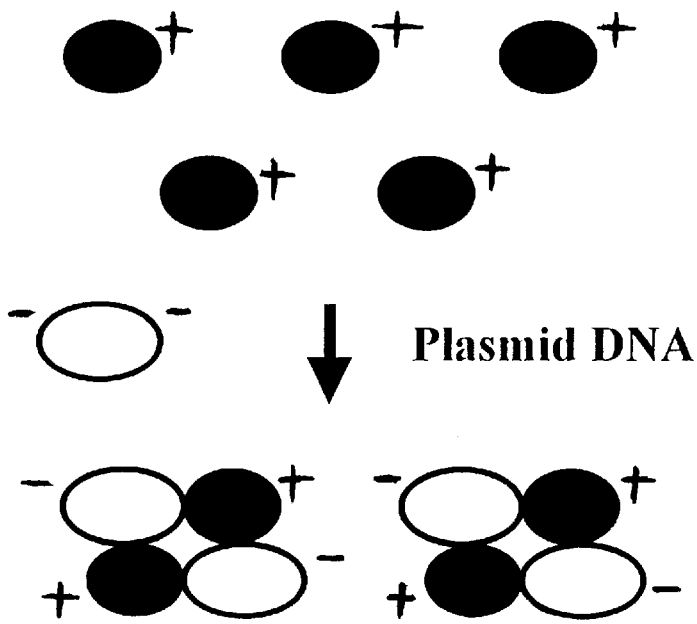

Dequalinium chloride: 0.1 mmol (53 mg) is dissolved in 20 ml of methanol in a 100-ml round bottom flask. The methanol is removed by the use of a rotary evaporator at elevated temperatures (40° C.) resulting in a thin, well-dispersed film in the bottom of the flask. Sterile water (10 ml) is then added to the flask and sonicated with a probe sonicator (power) until the mixture is clear. This results in a 10-mM dispersion of the dequalinium chloride in water, a product we have termed DQAsomes. See FIG. 1.

EXAMPLE 2

DQAsomes Binding of Plasmid DNA

Plasmid DNA (pGL3 luciferase firefly with SV-40 promoter, Promega) was incubated with increasing amounts of DQAsomes for 30 minutes at room temperature to allow the binding of DNA to DQAsomes. Thereafter, "SYBR GREEN 1" (FMC) was added. The fluorescence was read 30 minutes later on a PE LS50B spectrometer with excitation at 497 nm, emission at 520 nm, and slit width 5 cm.

Figure 2:
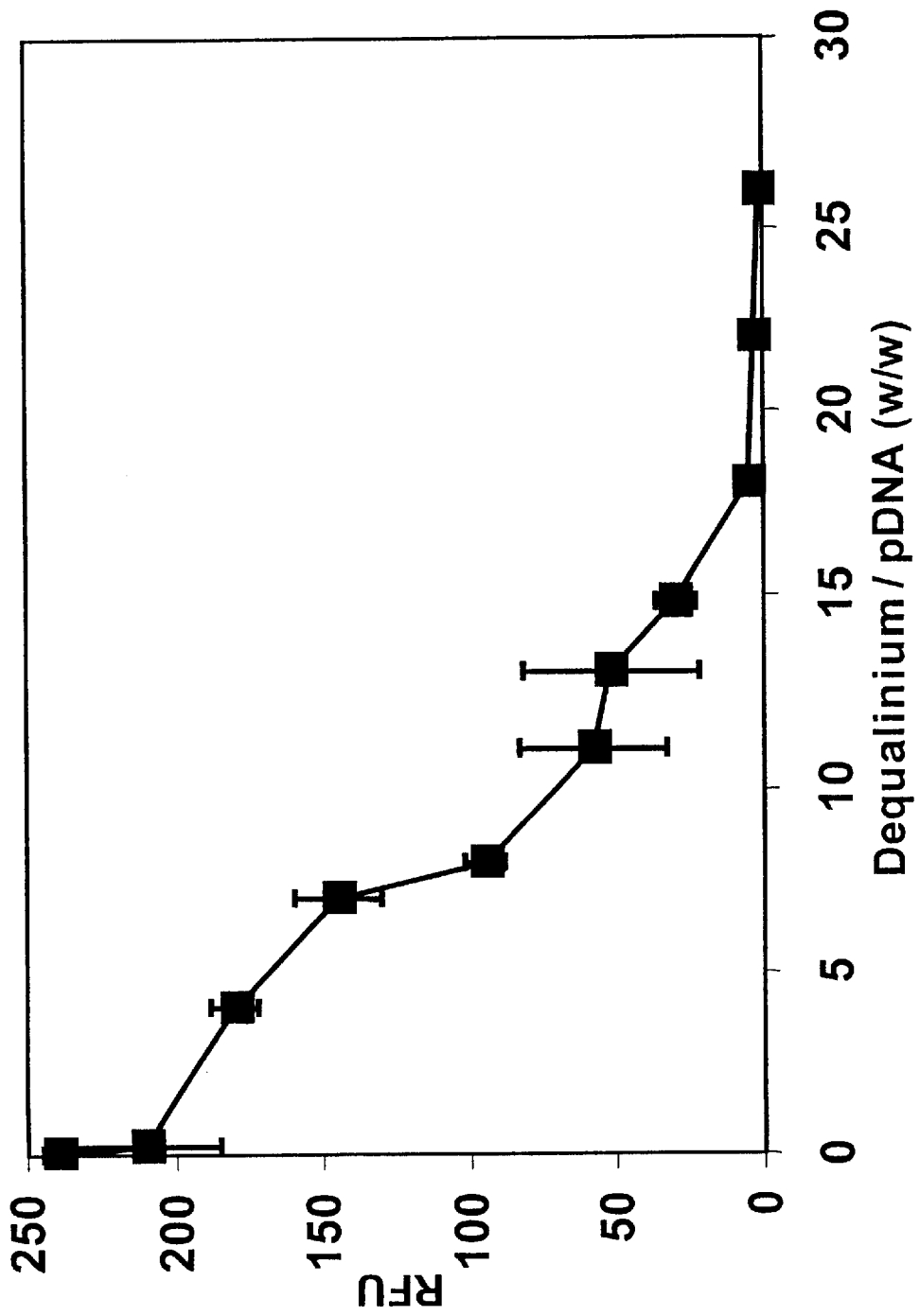
FIG. 2 shows the interaction of DNA and DQAsomes. This interaction is shown using a fluorescence-SYBR green method. In this procedure a decrease in fluorescence intensity is indicative of DNA/DQAsome interaction.

To assess the binding of DNA to DQAsomes the DNA specific dye "SYBR GREEN 1" was used. The fluorescent signal of this dye is greatly enhanced when bound to DNA; non-binding results in loss of fluorescence. As can be seen in FIG. 2, DQAsomes strongly interact with plasmid DNA. Increasing amounts of DQAsomes prevent "SYBR GREEN 1" from binding to the DNA, leading to a complete loss of the fluorescence signal.

EXAMPLE 3

Transfection of Cells Using DQAsomes as a Vector

Transfection of LLPKC 1 cells: cells were grown to 75% confluence in RPMI serum media with antibiotics before transfection. Transfection mixtures contained non-serum media and pDNA/liposome mixtures, which were allowed to sit for 30 minutes before use. As a model for transfection, plasmid DNA pGL3 luciferase firefly with SV-40 promoter (from Promega) was used. Each well received 15 $\mu$g of DNA and the appropriate amount of DQAsomes (total reaction volume 0.5 ml). Serum was removed and replaced with non-serum media. Cells were then incubated for one day before being washed with PBS and lysed with luciferase lysis buffer. Expression of the reporter gene was measured with a Moonlight luminometer, and protein was determined with a Pierce protein assay kit.

Figure 3:
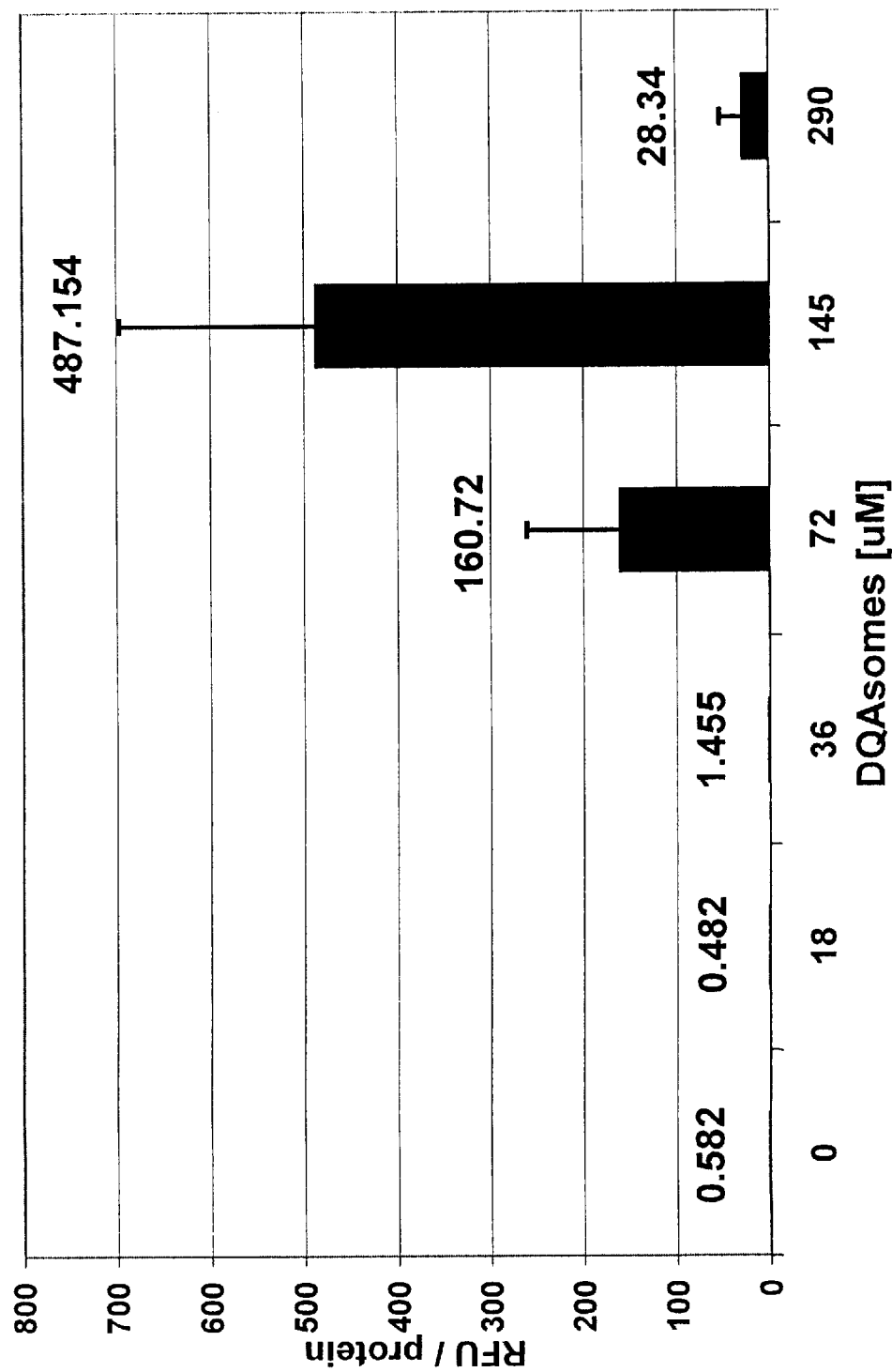
FIG. 3 shows the expression of reporter gene, firefly luciferase, measurable at an approximately equal mass ratio of DNA to dequalinium, corresponding to 72 $\mu$m DQAsomes.

The expression of the reporter gene firefly luciferase became measurable at an approximately equal mass ratio of DNA to dequalinium, corresponding to 72 μμM DQAsomes (FIG. 3). Doubling the amount of DQAsomes further increased the expression, whereas at a mass ratio of dequalinium to DNA of 1:4, the expression was drastically decreased. These results clearly demonstrate intracellular DNA delivery using DQAsomes as a vector.

EXAMPLE 4

Comparison of the Transfection Efficiency Between DQAsomes and DOTAP

Figure 4:
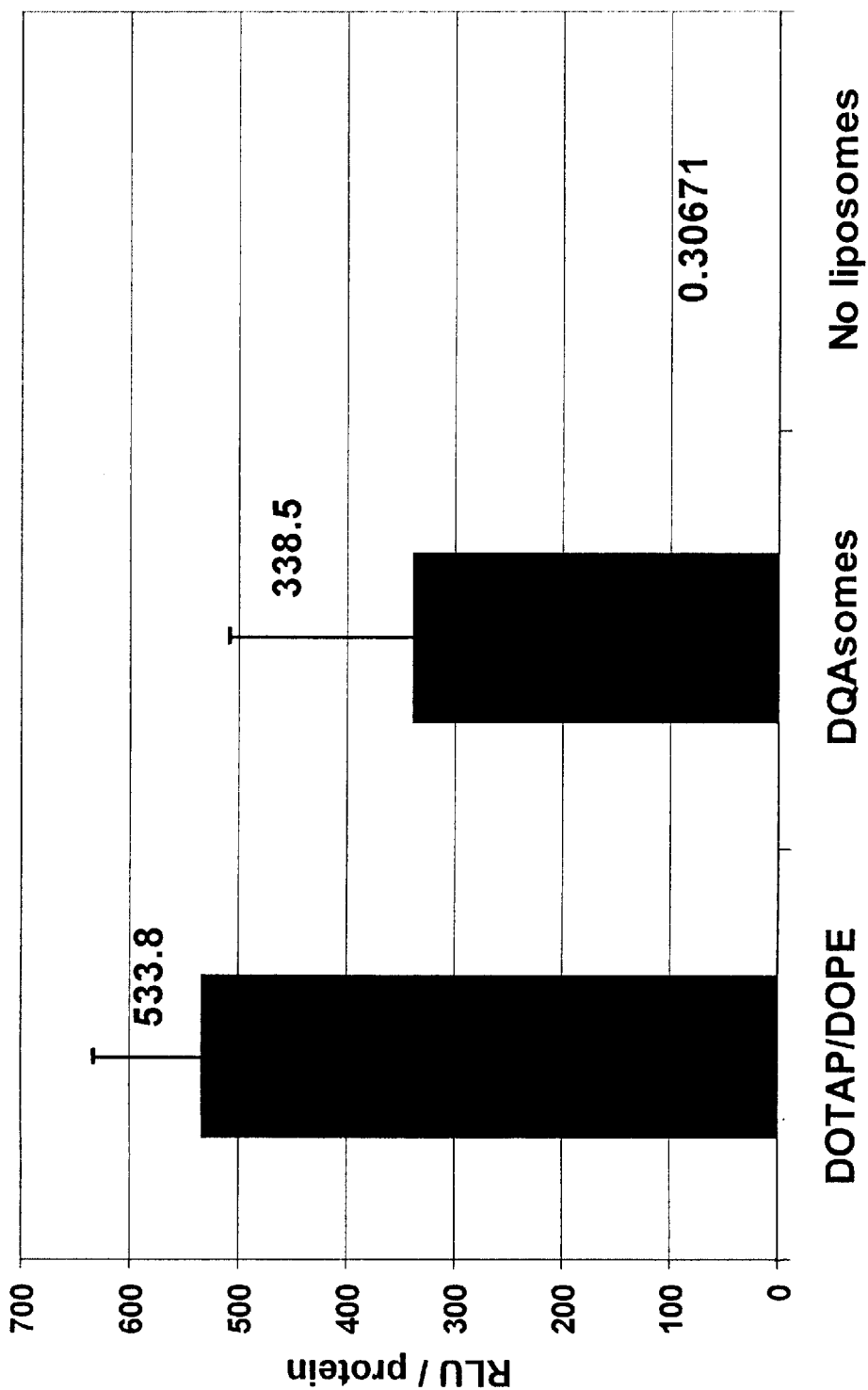
FIG. 4 shows a comparison of the transfection efficiency between DQAsomes and DOTAP.

The transfection of LLPKC 1 cells was done as disclosed in Example 3. FIG. 4 shows a comparison of the transfection efficiency between DQAsomes and the widely-used DOTAP. The DQAsomal system has a transfection efficiency in the range of the commercially available DOTAP vector.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A complex comprising DNA and a molecule which comprises two positive charge centers separated by a hydrocarbon chain wherein said hydrocarbon chain has about 8 to about 20 carbons and wherein said molecule with two positive charge centers is a salt of dequalinium.

2. The complex, according to claim 1, wherein said salt is selected from the group consisting of the acetate salt and the chloride salt.

3. The complex, according to claim 1, wherein said DNA is plasmid DNA.

* * * * *

UNITED STATES PATENT AND TRADEMARK OFFICE
CERTIFICATE OF CORRECTION

PATENT NO. : 6,090,619

DATED : July 18, 2000

INVENTOR(S) : Volkmar Weissig, et al.

It is certified that error appears in the above-identified patent and that said Letters Patent is hereby corrected as shown below:

Column 1, line 55: "Guinther," should read --Günther,--.

Column 2, line 12: "mitochondriaby" should read --mitochondria by--.

Column 3, line 57: "subj ect" should read --subject--.

Column 4, line 20: "DOAsomes" should read --DQAsomes--.

Column 4, line 33: "DOAsomes" should read --DQAsomes--.

Column 4, line 53: "DOAsomes" should read --DQAsomes--.

Column 5, line 3: "72 $\mu\mu$M" should read --72 $\mu$M--.

Signed and Sealed this

Seventeenth Day of April, 2001

NICHOLAS P. GODICI

Attest:

Attesting Officer

Acting Director of the United States Patent and Trademark Office